(12) United States Patent
Beliën et al.

(10) Patent No.: US 7,666,670 B2
(45) Date of Patent: Feb. 23, 2010

(54) ANIMAL MODEL FOR THE FAST IDENTIFICATION OF PHARMACEUTICAL ACTIVE COMPOUNDS IN VIVO

(75) Inventors: Ann Trudo Josée Beliën, Kermt (BE); Janine Arts, Breda (NL); Ann Odette Adolf Mariën, Schoten (BE); Annemie Francine Valckx, Lille (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/547,518

(22) PCT Filed: Mar. 3, 2004

(86) PCT No.: PCT/EP2004/002195

§ 371 (c)(1),
(2), (4) Date: Aug. 29, 2005

(87) PCT Pub. No.: WO2004/078985

PCT Pub. Date: Sep. 16, 2004

(65) Prior Publication Data

US 2006/0147377 A1 Jul. 6, 2006

(30) Foreign Application Priority Data

Mar. 5, 2003 (WO) .................. PCT/EP03/02264

(51) Int. Cl.
*C12N 5/10* (2006.01)
*C07H 21/04* (2006.01)
(52) U.S. Cl. .................. 435/325; 536/24.1
(58) Field of Classification Search .......... 536/24.1; 435/325
See application file for complete search history.

(56) References Cited

U.S. PATENT DOCUMENTS

2002/0197676 A1* 12/2002 Lukyanov et al. .......... 435/69.1
2003/0228627 A1* 12/2003 Emerson et al. .............. 435/7.1

FOREIGN PATENT DOCUMENTS

| WO | 94/16080 | 7/1994 |
| WO | 97/18841 | 5/1997 |
| WO | 02/055742 | 7/2002 |

OTHER PUBLICATIONS

Zitvogel et al, Human Gene Therapy 5(12): 1493-1506, 1994. Abstract only.*
Kuo et al, Exp. Cell. Res Exp. Cell Res. (2007), doi:10.1016/j.yexcr.2007.02.010.*
Tang et al, J. Biol. Chem 273(44): 29156-29163, 1998.*
Sowa et al, Ann. N. Y. Acad. Sci. 886: 195-199, 1999.*
Margueron et al, J. Mol. Endocrinol. 32: 583-594, 2004.*
Elbendary et al, Cell Growth and Differentiation 5: 1301-1307, 1994.*
Nie et al., "A facile and effective screening method for p21WAF1 promoter activators from microbial metabolites", The Journal of Antibiotics, vol. 54, No. 10, pp. 783-788 (2001).
Shinagawa et al., "Evaluation of the chemosensitivity of head and neck cancer cells based on the diverse function of mutated-p53", International Journal of Oncology, vol. 22, No. 2, pp. 383-389 (2003).
Park et al., "P53 Transactivation through various p53-responsive elements", Molecular Carcinogenesis, vol. 16, No. 2, pp. 101-108 (1996).
Wang et al., "HIPK2 overexpression leads to stabilization of p53 protein and increased p53 transcriptional activity by decreasing Mdm2 protein levels", BMC Molecular Biology, vol. 2, No. 8, pp. 1-9 (2001).
Doubrovin et al., "Imaging transcriptional regulation of p53-dependent genes with positron emission tomography in vivo", Proceedings of the National Academy of Sciences of the United States of America, vol. 98, No. 16, pp. 9300-9305 (2001).
Khanna et al., "Cyclosporine induces the expression of the cyclin inhibitor p21", Transplantation, vol. 67, No. 9, pp. 1262-1268 (1999).
International Search Report dated Jul. 5, 2004 for related International Application No. PCT/EP2004/002195.

* cited by examiner

*Primary Examiner*—Joseph Woitach
*Assistant Examiner*—Kevin K. Hill (57) ABSTRACT

In a first aspect the present invention provides a tumor cell line stably transfected with an expression vector containing a reporter gene, preferably a fluorescent protein, operably linked to a promotor that also controls expression of a protein that is associated with tumor regression, stabilization of tumor growth or inhibition of metastatic growth, characterized in that said cell line is capable to form a tumor when implanted or injected into the non-human animal. Compared to the traditional in vivo models, the present invention differs in that the reporter gene is not constitutively expressed, but only after exposure to a test compound that results in the expression of a protein or enzyme associated with tumor regression, stabilization of tumor growth or inhibition of metastatic growth. Only when a compound to be tested got into circulation and infiltrated the tumor it may generate the reporter signal, provided it promotes the expression of a protein associated with tumor regression and the promoter of said protein is operably linked to the reporter gene.

4 Claims, 4 Drawing Sheets

SEQUENCE LISTING

<160> NUMBER OF SEQ ID NOS: 14

<210> SEQ ID NO 1
<211> LENGTH: 1279
<212> TYPE: DNA
<213> ORGANISM: Artificial sequence
<220> FEATURE:
<223> OTHER INFORMATION: 1300bp fragment of the p21 promoter sequence
      from position -1300 to +88 relative to the TATA box

<400> SEQUENCE: 1
ggtaccggta gatgggagcg gatagacaca tcactcattt ctgtgtctgt cagaagaacc      60
agtagacact tccagaattg tcctttattt atgtcatctc cataaaccat ctgcaaatga     120
gggttatttg gcattttgt cattttggaa ccacagaaat aaaggatgac aagcagagag      180
ccccgggcag gaggcaaaag tcctgtgttc caactatagt catttctttg ctgcatgatc     240
tgagttaggt caccagactt ctctgagccc cagtttcccc agcagtgtat acgggctatg     300
tggggagtat tcaggagaca gacaactcac tcgtcaaatc ctccccttcc tggccaacaa     360
agctgctgca accacagggg tttcttctgt tcaggtgagt gtagggtgta gggagattgg     420
ttcaatgtcc aattcttctg tttccctgga gatcaggttg ccctttttg gtagtctctc     480 caattccctc cttcccggaa gcatgtgaca atcaacaact ttgtatactt aagttcagtg     540
gacctcaatt tcctcatctg tgaaataaac gggactgaaa aatcattctg gcctcaagat    600

```
gctttgttgg ggtgtctagg tgctccaggt gcttctggga gaggtgacct agtgagggat    660
cagtgggaat agaggtgata ttgtggggct tttctggaaa ttgcagagag gtgcatcgtt    720
tttataattt atgaattttt atgtattaat gtcatcctcc tgatcttttc agctgcattg    780
ggtaaatcct tgcctgccag agtgggtcag cggtgagcca gaaaggggc tcattctaac    840 agtgctgtgt cctcctggag agtgccaact cattctccaa gtaaaaaaag ccagatttgt    900
ggctcacttc gtggggaaat gtgtccagcg caccaacgca ggcgagggac tggggagga    960 gggaagtgcc ctcctgcagc acgcgaggtt ccgggaccgg ctggcctgct ggaactcggc   1020
caggctcagc tgctccgcgc tgggcagcca ggagcctggg ccccggggag ggcggtcccg   1080
ggcggcgcgg tgggccgagc gcgggtcgcc tccttgaggc gggcccgggc ggggcggttg   1140
tatatcaggg ccgcgctgag ctgcgccagc tgaggtgtga gcagctgccg aagtcagttc   1200
cttgtggagc cggagctggg cgcggattcg ccgaggcacc gaggcactca gaggaggtga   1260
gagagcggcg gcactcgag                                                1279

<210> SEQ ID NO 2
<211> LENGTH: 17
<212> TYPE: DNA
<213> ORGANISM: Artificial sequence
<220> FEATURE:
<223> OTHER INFORMATION: P21 specific forward primer

<400> SEQUENCE: 2
gagggcgcgg tgcttgg                                                     17

<210> SEQ ID NO 3
<211> LENGTH: 18
<212> TYPE: DNA
<213> ORGANISM: Artificial Sequence
<220> FEATURE:
<223> OTHER INFORMATION: p21 specific reverse primer

<400> SEQUENCE: 3
tgccgccgct ctctcacc                                                    18

<210> SEQ ID NO 4
<211> LENGTH: 26
<212> TYPE: DNA
<213> ORGANISM: Artificial Sequence
<220> FEATURE:
<223> OTHER INFORMATION: p21 specific forward primer

<400> SEQUENCE: 4
tcgggtaccg agggcgcggt gcttgg                                           26

<210> SEQ ID NO 5
<211> LENGTH: 27
<212> TYPE: DNA
<213> ORGANISM: Artificial Sequence
<220> FEATURE:
<223> OTHER INFORMATION: p21 specific reverse primer

<400> SEQUENCE: 5
atactcgagt gccgccgctc tctcacc                                          27

<210> SEQ ID NO 6
<211> LENGTH: 35
<212> TYPE: DNA
<213> ORGANISM: Artificial Sequence
<220> FEATURE:
```

```
<223> OTHER INFORMATION: p21 specific forward primer

<400> SEQUENCE: 6
tcgggtaccg gtagatggga gcggatagac acatc                          35

<210> SEQ ID NO 7
<211> LENGTH: 27
<212> TYPE: DNA
<213> ORGANISM: Artificial Sequence
<220> FEATURE:
<223> OTHER INFORMATION: p21 specific reverse primer

<400> SEQUENCE: 7
atactcgagt gccgccgctc tctcacc                                   27

<210> SEQ ID NO 8
<211> LENGTH: 46
<212> TYPE: DNA
<213> ORGANISM: Artificial Sequence
<220> FEATURE:
<223> OTHER INFORMATION: p53RE forward primer

<400> SEQUENCE: 8
ccctgcctgg acttgcctgg gtcgaccctg cctggacttg cctggc              46

<210> SEQ ID NO 9
<211> LENGTH: 54
<212> TYPE: DNA
<213> ORGANISM: Artificial Sequence
<220> FEATURE:
<223> OTHER INFORMATION: p53RE reverse primer

<400> SEQUENCE: 9
tcgagccagg caagtccagg cagggtcgac ccaggcaagt ccaggcaggg agct      54

<210> SEQ ID NO 10
<211> LENGTH: 47
<212> TYPE: DNA
<213> ORGANISM: Artificial Sequence
<220> FEATURE:
<223> OTHER INFORMATION: p53 RE promoter element

<400> SEQUENCE: 10
tccctgcctg gacttgcctg ggtcgaccct gcctggactt gcctggc              47

<210> SEQ ID NO 11
<211> LENGTH: 20
<212> TYPE: DNA
<213> ORGANISM: Artificial Sequence
<220> FEATURE:
<223> OTHER INFORMATION: HSV-TK forward primer

<400> SEQUENCE: 11
gtaccgagct cttacgcgtg                                           20

<210> SEQ ID NO 12
<211> LENGTH: 26
<212> TYPE: DNA
<213> ORGANISM: Artificial Sequence
<220> FEATURE:
<223> OTHER INFORMATION: HSV-TK reverse primer

<400> SEQUENCE: 12
gtggatccct gcttcatccc cgtggc                                    26
```

```
<210> SEQ ID NO 13
<211> LENGTH: 256
<212> TYPE: DNA
<213> ORGANISM: Artificial Sequence
<220> FEATURE:
<223> OTHER INFORMATION: p53RE_TK minimal promoter

<400> SEQUENCE: 13
aggtaccgag ctccctgcct ggacttgcct gggtcgaccc tgcctggact tgcctggctc      60
gagatctgcc gccccgactg catctgcgtg ttcgaattcg ccaatgacaa gacgctgggc     120
ggggtttgtg tcatcataga actaaagaca tgcaaatata tttcttccgg ggacaccgcc     180
agcaaacgcg agcaacgggc cacggggatg aagcagggat ctgcgatcta agtaagctga     240
tccaccggtc gccacc                                                    256

<210> SEQ ID NO 14
<211> LENGTH: 952
<212> TYPE: DNA
<213> ORGANISM: Artificial Sequence
<220> FEATURE:
<223> OTHER INFORMATION: p53RE_TK-ZsGreen insert used in the pGL3 basic
      vector

<400> SEQUENCE: 14
aggtaccgag ctccctgcct ggacttgcct gggtcgaccc tgcctggact tgcctggctc      60
gagatctgcc gccccgactg catctgcgtg ttcgaattcg ccaatgacaa gacgctgggc     120
ggggtttgtg tcatcataga actaaagaca tgcaaatata tttcttccgg ggacaccgcc     180
agcaaacgcg agcaacgggc cacggggatg aagcagggat ctgcgatcta agtaagctga     240
tccaccggtc gccaccatgg cccagtccaa gcacggcctg accaaggaga tgaccatgaa     300
gtaccgcatg gagggctgcg tggacggcca caagttcgtg atcaccggcg agggcatcgg     360 ctacccttc aagggcaagc aggccatcaa cctgtgcgtg gtggagggcg cccccttgcc     420
cttcgccgag gacatcttgt ccgccgcctt catgtacggc aaccgcgtgt tcaccgagta     480
cccccaggac atcgtcgact acttcaagaa ctcctgcccc gccggctaca cctgggaccg     540
ctccttcctg ttcgaggacg gcgccgtgtg catctgcaac gccgacatca ccgtgagcgt     600
ggaggagaac tgcatgtacc acgagtccaa gttctacggc gtgaacttcc ccgccgacgg     660
ccccgtgatg aagaagatga ccgacaactg ggagccctcc tgcgagaaga tcatcccgt      720 gcccaagcag ggcatcttga agggcgacgt gagcatgtac ctgctgctga aggacggtgg     780
ccgcttgcgc tgccagttcg acaccgtgta caaggccaag tccgtgcccc gcaagatgcc     840
cgactggcac ttcatccagc acaagctgac ccgcgaggac cgcagcgacg ccaagaacca     900
gaagtggcac ctgaccgagc acgccatcgc ctccggctcc gccttgccct ga            952
```

ANIMAL MODEL FOR THE FAST IDENTIFICATION OF PHARMACEUTICAL ACTIVE COMPOUNDS IN VIVO

CROSS REFERENCE TO RELATED APPLICATIONS

This application is a national stage application of Patent Application No. PCT/EP04/02195, filed Mar. 3, 2004, which application claims priority from Patent Application No. PCT/EP03/02264, filed Mar. 3, 2003, each of which is hereby incorporated by reference.

This invention relates to an animal model for neoplastic growth, in particular cancerous growth. Specifically, the animal model allows for the identification of pharmaceutical active compounds in vivo, comprising the use of tumor cells stably transfected with an expression vector comprising a reporter gene operably linked to a promoter that also controls expression of a protein associated with tumor regression, stabilization of tumor growth or inhibition of metastasis.

BACKGROUND OF THE INVENTION

There has long been a need for a representative animal model to test the efficacy of proposed new anti-neoplastic agents without having to perform long term xenograft studies. The present in vivo models with which potential anti-neoplastic agents are tested involve inplanting tumor cells into a non-human animal, treating the animal with the proposed new anti-neoplastic agent, and then monitoring the animals to determine the effect of treatment on the growth of the tumor. To aid the visualization of the tumor cells against the background of the host cells, many in vivo models use tumor cells stably transfected with a reporter gene such as the luciferase family and aequorin family of bioluminescent molecules.

A major drawback of these in vivo models, in the development of antitumor agents, is the limited troughput, i.e. a large number of animals and a large amount of proposed antitumor compound are required. Furthermore, these in vivo models are time consuming, as they require sufficient time for the implanted tumor to grow in the animal. Accordingly, an improved model was recently proposed by Lassota P. in the International Patent Application (PCT/EP02/00106) published as WO 02/055742 on 18 Jul. 2002. In this model the tumor cells with a reporter gene, which is activated by the antitumoral agent, are grown in a biocompatible semi-permeable encapsulation device, which is implanted in the non-human animal and removed after exposure of the animal to the compound to be tested. However, in view of the artificial environment of the tumor cells it is questionable whether the response of the tumor cells truly mimics the in vivo situation where a compound needs to get into circulation, infiltrate the tumor tissue and exert its biological effect.

Hence, to fulfil the need for an animal model for human neoplastic disease, which is without the above-mentioned deficiencies, the present invention discloses a new animal model that has the ability to truly mimic the pharmacological activity of a proposed anti-neoplastic compound in vivo. A model that allows monitoring the anti-neoplastic activity of a compound in a non-invasive way and that comprises the use of stably transformed tumor cells, which had been transfected with an expression vector containing a reporter gene operably linked to a promoter that also controls expression of a protein that is associated with tumor regression. In order to provide the desired animal model, the cells should;

retain the capability to form a tumor when implanted or injected into the animal;
generate a signal that parallels the endogenous response of a protein associated with tumor regression;
generate a signal with a good signal to noise ratio, to allow a real time analysis of the kinetic effect of drug substances in vivo;
generate a signal with a good reproducibility to provide a low variability between animals; and
generate a signal that allows non-invasive imaging of the induced response.

SUMMARY OF THE INVENTION

In a first aspect the present invention provides a tumor cell line stably transfected with an expression vector containing a reporter gene, preferably a fluorescent protein, operably linked to a promotor that also controls expression of a protein that is associated with tumor regression, characterised in that said cell line is capable to form a tumor when implanted or injected into the non-human animal.

Compared to the traditional in vivo models, the present invention differs in that the reporter gene is not constitutively expressed, but only after exposure to a test compound that results in the expression of a protein or enzyme associated with tumor regression. Only when a compound to be tested got into circulation and infiltrated the tumor it may generate the reporter signal, provided it promotes the expression of a protein associated with tumor regression and the promoter of said protein is operably linked to the reporter gene.

The model is highly advantageous over prior in vivo models, since the turnover time to test the in vivo pharmaceutical activity of proposed anti-neoplastic compounds is reduced. In the traditional in vivo models it typically takes 4 to 5 weeks to obtain a result, in the present model, once the tumor is formed in the non-human animal, it is possible to see the effects of a test compound in a couple of days. Further, in view of the brightness and reproducibility of the fluorescent signal, the tumors can be seen through the skin and measured using an automated whole-body imaging system. As a consequence a lower number of animals is needed to obtain statistical significant effects. A further advantage of the present animal model is the sensitivity, and responsiveness of the fluorescent signal within a broad concentration range of test compound. This combination allows performing a kinetic real-time analysis for the in vivo activity of the test compound and to predict the antitumoral efficacy of the test compound when combined with the change in tumor weight as observed. This combination of characteristics allows non-invasive imaging after limited amounts of dosing with the test compound (4 days instead of the traditional period of 30 days), leading to decrease in experimental time and thus test compound, as well as to a decrease in animal suffering and occupation of animal facilities.

In a particular embodiment the promoter consists of the p21 promoter. The p21 protein acts as an inhibitor of cyclin-dependent kinase activity and effectively stops cell-cycle progression. It has been shown a wide variety of anti-tumoral agents activate the p21 promoter, including DNA damaging agents and histone deacetylase inhibitors that activate the p21 promoter through the p53 responsive element (located at the −4500 bp to −1300 bp region relative to the TATA box) or sp1 sites (located at the −60 bp to +40 bp region relative to the TATA box), respectively and leading to increased expression of the p21 protein. In a particular embodiment of the present invention the p21 promoter consists of a p21 1300 bp promoter fragment characterised in that said promoter fragment, does not comprise the p53 responsive elements and accordingly is non-responsive to DNA damaging agents. In another embodiment the p21 promoter consists of a p21 promoter comprising the p53 responsive elements, said p21 promoter being responsive to DNA damaging agents. Alternatively the promoter responsive to DNA damaging agents consists of a minimal promoter such as the thymidine kinase basal promoter of the herpes simplex virus (HSV-TK) comprising at least one p53 responsive element. Accordingly, based on the promoter used, the present invention provides a model selective for the in vivo pharmacological effects of either DNA damaging agents and/or of histone deacetylase inhibitors. Or in general, depending on the neoplastic agents of interest, alternative response elements could be used.

It is also an object of the present invention to provide an in vitro method of screening a compound for anti-neoplastic activity, comprising the steps of:

contacting the tumor cells according to the invention with the compound to be tested; and measure the expression of the reporter gene;

wherein an increase of reporter gene expression compared to the control levels identifies the compound as having anti-neoplastic activity. In a particular embodiment the reporter gene is a fluorescent protein and the expression of the reporter gene is measured as the amount of fluorescent light emitted. As explained above, also for this in vitro method it is possible to alter the selectivity of the screen depending on the promoter used. In a specific embodiment of the present invention the in vitro screening method is selective for histone deacetylase inhibitors and comprises tumor cells stably transfected with an expression vector comprising a p21 1300 bp promoter fragment characterised in that said promoter fragment does not comprise the p53 responsive elements. In a further embodiment the in vitro screening method is selective for DNA damaging agents such as for example actinomycinD, and comprises tumor cells stably transfected with an expression vector comprising at least one p53 responsive element. In one embodiment the expression vector comprises the p53 responsive element consisting of SEQ ID No.10., preferably as part of a minimal promoter such as the HSV-TK promoter.

In a further embodiment the present invention provides non-human animals for screening the pharmaceutical activity of a compound, said animal comprising a stably transformed tumor cell according to the invention. Said tumor cells could be surgically implanted or injected as a tumor cell suspension under the skin of the non-human animal to provide a subcutaneous model, into the organ of tumor origin (for example lung tumor cells into the lungs) to provide an orthotopic model, into the peritoneal cavity of the non-human animal to provide the peritoneal model, or into the blood vessels of the non-human animal to provide the metastasis model. In a preferred embodiment the tumor cells are injected subcutaneously to provide the subcutaneous model.

It is thus an object of the present invention to provide a method of screening a compound for pharmaceutical activity, comprising the steps of:

administering tumor cells according to the invention to a non-human animal in an amount sufficient to effect production of a tumor in said non-human animal;

allowing the tumor cells sufficient time to form a tumor in said non-human animal;

administering a potentially active compound to said non-human animal; and evaluate the effect of said compound on the tumor cells by measuring the expression of the reporter gene.

Incubation with pharmaceutical active compounds will result in an increase of reporter gene expression compared to the control levels.

This and further aspects of the present invention will be discussed in more detail hereinafter.

BRIEF DESCRIPTION OF THE DRAWING

FIG. 1 A: Dose response of the p21 promoter construct to DNA damaging agents and histone deacetylase inhibitors (HDACi) of clone 1. Cells are treated for 24 h with the indicated compounds, i.e. the DNA damaging agents campthotecin (camp.), bleomycin (bleo) and doxorubicin (dox) and the HDACi compounds TSA (trichostatin A,) Mitsui, compound X and SAHA (suberoylanilide hydroxamic acid). Fluorescence was measured using the Ascent Fluoroskan as described in M&M. Fold induction was calculated as fluorescence after induction divided by fluorescence of DMSO treated cells. Clone 1 showed a 5-fold induction after treatment with $10^{-7}$M TSA; 2-fold induction to $10^{-6}$M Mitsui and 3-fold induction to $10^{-6}$M compound X.

FIG. 1 B: Dose response of the p21 promoter construct to DNA damaging agents and histone deacetylase inhibitors (HDACi) of clone 5. Cells are treated for 24 h with the indicated compounds, i.e., the DNA damaging agents campthotecin (camp.), bleomycin (bleo) and doxorubicin (dox) and the HDACi compounds TSA, Mitsui, compound X and SAHA. Fluorescence was measured using the Fluoroskan as described in M&M. Fold induction was calculated as fluorescence after induction divided by fluorescence of DMSO treated cells. Clone 5 showed a 5-fold induction after treatment with $10^{-7}$M TSA; 2-fold induction to $10^{-6}$M Mitsui and 4-fold induction to $10^{-6}$M compound X.

FIG. 2. In vivo visualisation of xenograft fluorescence. Clone 1 was subcutaneous injected ($10^7$ cells/200 µl) into the flank of nude mice. From day 12 on, animals were dosed daily during 6 days with Solvent, Mitsui (20 mpk) or compound X (40 mpk). Tumors in living mice were evaluated for fluorescence the in house developed Automated Whole Body Imaging System and fluorescence intensity was compared. Induction of ZsGreen was very clear 3 days after administration of the first dose and reached a plateau 5 days after starting the treatment.

FIG. 4A shows p21 protein induction of clone 5 as measured using a p21 ELISA. FIG. 4B represents the induced fluorescence in clone 5 as measured using the Ascent Fluoroskan. The induction patern for p21 is identical to the induction patern of the p21 responsive ZsGreen expression vector pG13-basic-ZsGreen-1300.

FIG. 5. $p21^{waf,cip1}$ promoter-ZsGreen model predicts antitumoral effect of MS-275 in individual mice in vivo. Nude mice were injected subcutaneously with human A2780p21$^{waf, cip1}$ ZsGreen ovarian tumor cells (107 cells/mouse) and from day 4 subsequently treated p.o. with vehicle (control group, 20% hydroxypropyl-β-cyclodextrin) or MS-275 (QD) at the indicated doses. Tumor weight and fluorescence of individual tumors was evaluated on day 28, using the Automated Whole Body Imaging System.

DETAILED DESCRIPTION

Vectors

The present invention relates to a vector comprising a reporter gene operably linked to a promoter that also controls the expression of a protein or enzyme the expression level of which is associated with a physiological condition.

Operably linked as used herein, means functionally fusing a promoter with a gene in the proper frame to express the gene under control of the promoter. As used herein, the term "reporter gene" means a gene encoding a gene product that can be identified using simple, inexpensive methods or reagents and that can be operably linked to the promoter region or an active fragment thereof. Reporter genes such as, for example, a firefly luciferase, β-galactosidase, alkaline phosphatase, the bacterial chloramphenicol acetyl transferase or a fluorescent protein reporter gene, can be used to determine transcriptional activity in screening assays according to the invention (see, for example, Goeddel (ed.), Methods Enzymol., Vol. 185, San Diego: Academic Press, Inc. (1990); see also Sambrook, supra). In a preferred embodiment, the reporter gene is a fluorescent protein, in particular a fluorescent protein selected from the group consisting of EGFP, EYFP, DsRed, ZsGreen, ZsYellow, HcRed or destabilized fluorescent proteins such as pDsRed, pHcRed1, pd2EGFP or pd2EYFP. In a particular embodiment of the present invention the reporter gene is the fluorescent protein ZsGreen. Said reporter molecules and the gene sequences thereof are known in the art and are commercially available such as the fluorescent proteins sold by Clontech, San Diego, Calif.

The techniques and protocols for the manipulation of nucleic acid, for example in preparation of nucleic acid constructs, mutagenesis, sequencing, introducing of DNA into cells and gene expression, and analysis of proteins, are described in detail in Current Protocols in Molecular Biology, Ausbel et al. eds., John Wiley & Sons, 1997.

The vectors according to the invention can be chosen or constructed from commercially available vectors such as pCAT3, pGL2, pGL3 or pSV-β-Galactosidase and typically comprise appropriate regulatory sequences as well as one or more selectable marker genes, for example an ampicillin resistance gene in the case of a bacterial plasmid or a neomycin resistance gene for a mammalian vector. As exemplified hereinbelow, in one embodiment of the present invention the vector is constructed from the pGL3 basic vector. Said vector sequences are known in the art and commercially available such as the pGL3 basic vector sold by Promega, Madison, Wis. In particular the vectors of the present invention contain as one of the regulatory sequences a promoter sequence not only compatible with the host cell for which the expression vector is designed but also responsive to compounds, including proteins, peptides, oligonucleotides and small molecules, known to have a desired physiological effect in the respective host cell. Accordingly, the promoter sequence in the expression vectors of the present invention comprise at least one regulatory sequence element, also known as responsive element, characterized in that it regulates expression of the linked reporter gene and is activated due to the binding or release of a transcription factor, wherein the presence or absence of said transcription factor is correlated with the desired physiological condition of the host cell. For example, if the desired physiological condition consists of inducing cell cycle arrest and differentiation in the host cell, the promoter sequence may comprises the GC-rich motifs found in the proximal part of the $p21^{WAF-1/Cip1}$ promoter which are known to be activated upon exposure to p21 activators such as the transcription factors Sp1 and Sp3 as well as other inducers of cell cycle arrest and cell differentiation such as steroid hormones, nerve growth factor, tumor necrosis factor-α phorbol esters, phosphatase inhibitors, intereferon γ, and the Smad tumor suppressor proteins.

Accordingly, the promoter as used herein may either be a naturally occuring promoter, such as the $p21^{WAF-1/Cip1}$ promoter that also controls the expression of a protein the expression level of which is dependent on the desired physiological condition or fragments thereof having promoter activity such as the p21 1300 bp promoter fragment as described in the examples hereinafter. In a particular embodiment the promoter sequence consists of a recombinant DNA construct comprising one of the aforementioned regulatory sequence elements, such as the p53 responsive elements operably linked to minimal promoter elements such as the minimal interleukin 6 (IL6) promoter (phu.IL6Pluc+ Plaisance et al. (1997) MCB 17, 3733-3743), the minimal E1B promoter (pMCSluc commercially available from Stratagene) or the commercially available TK promoter for luciferase (pTKluc Promega), preferably the promoter consists of the p21 1300 bp promoter fragment as described hereinbelow, or of the HSV-TK minimal promoter comprising the p53 responsive element as decribed hereinbelow. In another embodiment the promoter sequence will be a promoter that also controls expression of a protein that is associated with tumor regression or a fragment thereof having promoter activity.

Target Cells

In another aspect the present invention relates to a target cell stably transformed with an expression vector comprising a reporter gene operably linked to a promoter that also controls the expression of a protein or enzyme the expression level of which is associated with a physiological condition.

The vector constructs as described above can be introduced into the target cells by means of any known method such as transfection or transduction, preferably using standard transfection methods such as liposomes, calcium phosphate precipitation, electroporation and use of a gene gun.

As it is a further aspect of the present invention to provide a non-human animal model for neoplastic growth, in particular cancerous growth the vectors according to the invention will be introduced in target cells capable to form a tumor when implanted or injected into the non-human animal. Examples of suitable cell lines include melanomas, lung tumor lines, renal tumor lines, colon tumor lines, prostate tumor lines, ovarian tumor lines, breast tumor lines, central nervous system tumor lines, leukemic cell lines, etc. In one embodiment the target cells consists of an ovarian tumor cell line, in particular A2780 (ECACC No. 93112520), in another embodiment the target cells consist of a colorectal carcinoma cell line, in particular HCT116 (ATCC No. CCL-247). Further target cells can be selected from various cell lines, which include various mammalian cell lines, especially human cell lines. It should be noted that the target cells as used herein, include any of the aforementioned cells, already transformed with an expression system for a selection marker such as neomycin, a therapeutic protein such as methioninase or a reporter gene product. For example, in an alternative embodiment of the invention, the target cells capable to form a tumor when administered to a non-human animal, are already transformed with an expression system encoding a reporter protein such as firefly luciferase or a fluorescent protein (see above). These cells may be transformed with an a vector according to the invention, provided the emission wavelengths of the luminescent proteins, i.e. the reporter gene providing the basal colour and the vector according to the invention providing the inducible colour, do not overlap with one another. Possible combinations include amongst others DsRed with the enhanced fluorescent proteins EBFP, ECEP, EGFP and EYFP; ZsGreen with DsRed; EGFP with EYFP; EGFP with EBFP; EBFP with EYIP; or ECFP with EYFP. Once transformed with the vectors according to the invention, these cells allow an efficient detection of the whole tumor, for example to establish when the administered tumor cells had sufficient time to form a tumor in said non-human animal, in combination with the inducible system described herein to study the anti-neoplastic activity of a test compound. In particular, to study whether the compound to be tested, enters the tumor via passive diffusion and/or angiogenesis. In any case the choice of the target cell will depend on the physiological condition to be investigated. Alternatively, the expression vector according to the invention has a low but detectable basal expression of the reporter gene with a good induction factor to reach significance. In this embodiment the low basal expression can be used to establish when the administered tumor cells had sufficient time to form a tumor in said non-human animal. Hence no double transfection of the target cells is required. This advantage embodiment occurred when the vector according to the invention comprises ZsGreen as reporter gene.

It is thus an object of the present invention to provide a stably transformed tumor cell line, which has been transfected with an expression vector containing a reporter gene operably linked to a promoter that also controls expression of a protein that is associated with tumor regression. In particular a stably transformed ovarian carcinoma cell line, preferably A2780 cells comprising an expression vector containing a nucleic acid sequence encoding a fluorescent protein operably linked to a promoter that is responsive to p21 activators, preferably said promoter comprising the 1300 bp p21 promoter sequence (SEQ ID No.1), even more preferably said promoter sequence consisting of the 1300 bp p 21 promoter sequence (SEQ ID No.1). Wherein in a further embodiment the fluorescent protein is selected from the group consisting of EGFP, EYFP, DsRed, ZsGreen, ZsYellow, HcRed or destabilized fluorescent proteins such as pDsRed, pHcRed1, pd2EGFP or pd2EYFP and in a specific embodiment the fluorescent protein consists of ZsGreen. In a preferred embodiment the stably transformed cells are selected from the clones deposited at the Belgian Coordinated Collection of Microorganisms (BCCM) on Jan. 20, 2003 as pGL3-basic-ZsGreen-1300-clone 1 and pGL3-basic-ZsGreen-1300-clone 2 with the respective accession numbers LMBP 5958CB and LMBP 5959CB. Said clones comprise an expression vector derived from the commercially available pGL3 vector and containing a nucleic acid sequence encoding ZsGreen operably linked to a promoter that is responsive to p21 activators, said promoter comprising the 1300 bp p21 promoter sequence (SEQ ID No.1), wherein said clones are characterized in that they have a low basal fluorescence expression which upon induction with known inducers of cell cycle arrest and cell differentiation such as Mitsui (a.k.a. MS-275—Shering—Registry Number 209783-80-2), allow detection of the fluorescence by means of an automated whole-body imaging system.

In view of these characteristics, i.e.
    capability to form a tumor when implanted or injected into a non-human animal,
    low basal fluorescence,
    a fluorescence which is inducible upon exposure to known inducers of cell cycle arrest and cell differentiation in a specific way, and
    that to a level detectable using non-invasive whole-body imaging techniques, said clones provide an important tool to study the in vivo pharmaceutical activity of proposed anti-neoplastic compounds. Compared to the traditional in vivo models, use of these cells in non-human animals, in particular laboratory animals such as rabbits, guinea pigs, mice, rats and dogs, preferably rodents, allow compounds to be evaluated at earlier time points in the drug discovery process without performing time and compound consuming pharmacokinetics (PK) and pharmacodynamics (PD) studies.

Figure 6:
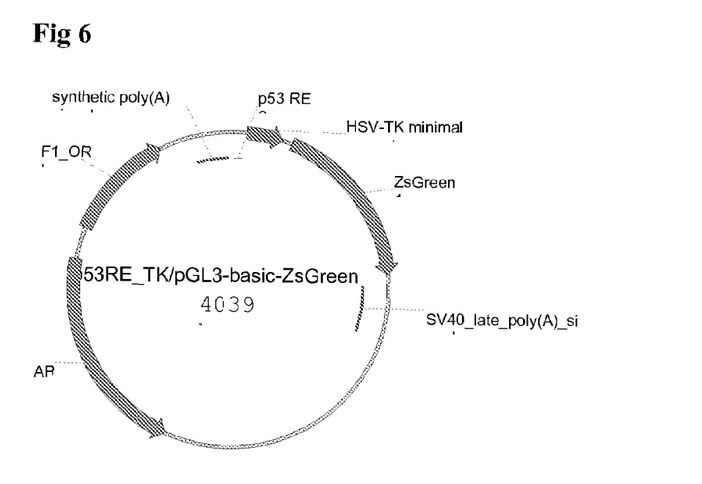
FIG. 6. 53RE_TK/pGL3-basic-ZsGreen expression vector

In an alternative embodiment the cell lines are transformed with an expression vector comprising a promoter sequence consisting of a recombinant DNA construct comprising one of the aforementioned regulatory sequence elements, such as the p53 responsive elements operably linked to minimal promoter elements such as the minimal interleukin 6 (IL6) promoter (phu.IL6Pluc+Plaisance et al. (1997) MCB 17, 3733-3743), the minimal E1B promoter (pMCSluc commercially available from Stratagene) or the commercially available TK promoter for luciferase (pTKluc Promega). In particular a stably transformed colorectal carcinoma cell line or ovarian carcinoma cell line, preferably HCT116 cells or A2780 cells comprising an expression vector containing an nucleic acid sequence encoding a fluorescent protein operably linked to a promoter that is responsive to p53 activators, preferably said promoter comprising the p53 responsive element (SEQ ID No.10), more preferably said promoter consisting of the minimal HSV-TK promoter comprising the p53 responsive element (Seq ID No.10), even more preferably consisting of the p53 responsive HSV-TK promoter sequence (SEQ ID No.13). Wherein in a further embodiment the fluorescent protein is selected from the group consisting of EGFP, EYFP, DsRed, ZsGreen, ZsYelow, HcRed or destabilized fluorescent proteins such as pDsRed, pHcRed1, pd2EGFP or pd2EYFP and in a specific embodiment the fluorescent protein consists of ZsGreen. In a particular embodiment the stably transformed cells consist of A2780 or HCT116 cells transfected with the p53RE_TK/pGL3-Basic-ZsGreen vector (Fig) derived form the commercially available pGL3 vector and containing a nucleic acid sequence encoding ZsGreen operably linked to a promoter that is responsive to p53 activators, said promoter comprising the p53 responsive HSV-TK promoter sequence (SEQ ID No.14), wherein said clones are characterized in that they have a low basal fluorescence expression which upon induction with p53 activators such as exposure to DNA damaging agents, hypoxia, nucleotide depletion or oncogenic activation allows detection of the fluorescence by means of an automated whole-body imaging system.

In view of these characteristics, i.e.
    capability to form a tumor when implanted or injected into a non-human animal,
    low basal fluorescence,
    a fluorescence which is inducible upon exposure to known inducers of cell cycle arrest and cell differentiation in a specific way, and
    that to a level detectable using non-invasive whole-body imaging techniques, said clones provide an important tool to study the in vivo pharmaceutical activity of proposed anti-neoplastic compounds. Compared to the traditional in vivo models, use of these cells in non-human animals, in particular laboratory animals such as rabbits, guinea pigs, mice, rats and dogs, preferably rodents, allow compounds to be evaluated at earlier time points in the drug discovery process without performing time and compound consuming pharmacokinetics (PK) and pharmacodynamics (PD) studies.

Accordingly, in a further embodiment the invention provides stably transformed tumor cell lines which have been transfected with an expression vector containing a reporter gene operably linked to a promoter sequence consisting of a recombinant DNA construct comprising a regulatory sequence element operably linked to a minimal promoter element, characterized in that said promoter sequence responds to compounds associated with tumor regression. Compounds as used herein includes proteins, peptides, oligonucleotides and small molecules.

Assays

It is also an object of the present invention to provide the use of the above mentioned cell lines in an in vitro screening assay to identify pharmaceutically active compounds, said method comprising contacting the stably transformed cells according to the invention with the compound to be tested;

and measure the expression of the reporter gene. Pharmaceutically active compounds as used herein refer to compounds capable to activate the promoter sequence present in the expression vector.

In the particular embodiment to identify compounds with anti-neoplastic activity, the stably transformed cells in the aforementioned screening method comprise an expression vector containing a reporter gene operably linked to a promoter sequence that is responsive to compounds associated with tumor regression. It is thus an object of the present invention to provide an in vitro method to identify compounds with anti-neoplastic activity, said method comprising; contacting stably transformed tumor cells according to the invention with the compound to be tested, and measure the expression of the reporter gene.

In a preferred embodiment of the aforementioned in vitro screening method, the stably transformed tumor cells consist of stably transformed ovarian carcinoma cells, preferably A2780 cells comprising an expression vector containing a nucleic acid sequence encoding a fluorescent protein operably linked to a promoter that is responsive to p21 activators, preferably said promoter comprising the 1300 bp p21 promoter sequence (SEQ ID No.1), even more preferably said promoter sequence consisting of the 1300 bp p 21 promoter sequence (SEQ ID No.1). Wherein in a further embodiment the fluorescent protein is selected from the group consisting of EGFP, EYFP, DsRed, ZsGreen, ZsYellow, HcRed or destabilized fluorescent proteins such as pDsRed, pHcRed1, pd2EGFP or pd2EYFP and in a specific embodiment the fluorescent protein consists of ZsGreen or ZsRed. In a more preferred embodiment the stably transformed tumor cells used in the in vitro screening method are selected from the clones deposited at BCCM with accession numbers LMBP 5958CB and LMBP 5959CB. In another embodiment of the aforementioned in vitro screening method, the stably transformed tumor cells consist of stably transformed colorectal carcinoma cells or stably transformed ovarian carcinoma cells, preferably A2780 cells or HCT116 cells, comprising an expression vector containing a nucleic acid sequence encoding a fluorescent protein operably linked to a promoter that is responsive to p53 activators, preferably said promoter comprising the p53 responsive element (SEQ ID No. 10), even more preferably said promoter consisting of the minimal HSV-TK promoter comprising the p53 responsive element (SEQ ID No. 13). Wherein in a further embodiment the fluorescent protein is selected from the group consisting of EGFP, EYFP, DsRed, ZsGreen, ZsYellow, HcRed or destabilized fluorescent proteins such as pDsRed, pHcRed1, pd2EGFP or pd2EYFP and in a specific embodiment the fluorescent protein consists of ZsGreen. In a particular embodiment the stably transformed cells used in the in vitro method consist of A2780 or HCT116 cells transfected with the the p53RE_TK/pGL3-Basic-ZsGreen vector (FIG. 6).

It will be readily appreciated by the skilled artisan, that the aforementioned assay can be adapted to high throughput screening purposes. For example the assays wherein anti-neoplastic activity is evaluated by measuring change in fluorescence can be designed around an instrument called a FLuorescence Imaging Plate Reader ((FLIPR®), Molecular Devices Corporation). In its most common configuration, it excites and measures fluorescence emitted by fluorescent compounds. It uses an argon-ion laser to produce high power excitation of a fluorophore, a system of optics to rapidly scan the over the bottom of a 96-/384-well plate and a sensitive, cooled CCD camera to capture the emitted fluorescence. It also contains a 96-/384-well pipetting head allowing the instrument to deliver solutions of test agents into the wells of a 96-/384-well plate. The FLIPR assay is designed to measure fluorescence signals from populations of cells before, during and after addition of compounds, in real time, from all 96-/384-wells simultaneously. The FLIPR assay may be used to screen for and characterise compounds functionally active in the stably transformed tumor cells according to the invention.

A high throughput screening assay, specifically usefull to identify p21 or p53 activators could consist of a single step arrangement wherein the ovarian carcinoma cells, in particular the A2780 cells stably transformed with an expression vector according to the invention, are incubated with a test compound and after sufficient time to allow interaction (8-24 hours, typically 12-24 hours, in particular 24 hours.) the change in relative fluorescence units measured using an automated fluorescence plate reader such as FLIPR or Ascent Fluoroskan (commercially available from Thermo Labsystems, Brussel, Belgium).

Non-human Animal Model

It is also an embodiment of the present invention to provide non-human animals comprising a target cell according to the invention. In particular to provide a non-human animal model for neoplastic growth, in particular cancerous growth.

Accordingly, the present invention provides a method to prepare a non-human animal model for neoplastic growth, said method comprising administering to said non-human animal an amount of stably transformed tumor cells according to the invention, sufficient to effect production of a tumor in said non-human animal. Wherein said non-human animal for use as models are preferably mammalian subjects, most preferably convenient laboratory animals such as guinea pigs, rabbits, rats, and mice and the like. For closer analogy to human subjects, primates could also be used. Particularly useful are subjects susceptible to tumor development, such as subjects with impaired immune systems, typically nude mice or SCID mice. Any appropriate vertebrate subject can be used, the choice being dictated mainly by convenience and similarity to the system of ultimate interest. The non-human animal model is preferably a rodent such as a nude mice and the amount of cells to effect production of a tumor typically ranges from $10^6$ to $10^8$ cells (see for example U.S. Pat. No. 6,251,384). Preferably such administration is subcutaneous and the tumors are formed as solid masses.

The above mentioned animal models can be used in a method for screening compounds with anti-neoplastic activity. Preferably the tumor cells administered to said non-human animal consist of stably transformed ovarian carcinoma cells, preferably A2780 cells comprising an expression vector containing a nucleic acid sequence encoding a fluorescent protein operably linked to a promoter that is responsive to p21 activators, preferably said promoter comprising the 1300 bp p21 promoter sequence (SEQ ID No.1), even more preferably said promoter sequence consisting of the 1300 bp p 21 promoter sequence (SEQ ID No.1). Wherein in a further embodiment the fluorescent protein is selected from the group consisting of EGFP, EYFP, DsRed, ZsGreen, ZsYellow, HcRed or destabilized fluorescent proteins such as pDsRed, pHcRed1, pd2EGFP or pd2EYFP and in a specific embodiment the fluorescent protein consists of ZsGreen or ZsRed. In a more preferred embodiment the stably transformed tumor cells used in the in vivo screening method are selected from the clones deposited at BCCM with accession numbers LMBP 5958CB and LMBP 5959CB.

In an alternative embodiment the tumor cells used in the in vivo screening method are transformed with an expression vector comprising a promoter sequence consisting of a recombinant DNA construct comprising one of the aforementioned regulatory sequence elements, such as the p53 responsive elements operably linked to minimal promoter elements such as the minimal interleukin 6 (IL6) promoter (phu.IL6Pluc+Plaisance et al. (1997) MCB 17, 3733-3743), the minimal E1B promoter (pMCSluc commercially available from Stratagene) or the commercially available TK promoter for luciferase (pTKluc Promega). In one embodiment the stably transformed tumor cells used in the in vivo screen consist of stably transformed colorectal carcinoma cells or stably transformed ovarian carcinoma cells, preferably A2780 cells or HCT116 cells, comprising an expression vector containing a nucleic acid sequence encoding a fluorescent protein operably linked to a promoter that is responsive to p53 activators, preferably said promoter comprising the p53 responsive element (SEQ ID No. 10), even more preferably said promoter consisting of the minimal HSV-TK promoter comprising the p53 responsive element (SEQ ID No. 13). Wherein in a further embodiment the fluorescent protein is selected from the group consisting of EGFP, EYFP, DsRed, ZsGreen, ZsYellow, HcRed or destabilized fluorescent proteins such as pDsRed, pHcRed1, pd2EGFP or pd2EYFP and in a specific embodiment the fluorescent protein consists of ZsGreen. In a particular embodiment the stably transformed cells used in the in vivo method consist of A2780 or HCT116 cells transfected with the p53RE_TK/pGL3-Basic-ZsGreen vector (FIG. 6).

Accordingly, in a further embodiment the invention provides the use of stably transformed tumor cell lines which have been transfected with an expression vector containing a reporter gene operably linked to a promoter sequence consisting of a recombinant DNA construct comprising a regulatory sequence element operably linked to a minimal promoter element, characterized in that said promoter sequence responds to compounds associated with tumor regression, in an in vivo screening method according to the invention.

When used in in vivo screening methods the stably transformed tumor cells administered to said non-human animal should have had sufficient time to form a tumor in said non-human animal. A tumor and in particular a caliper measurable solid tumor is typically formed 7-20 days after the administration of the stably transformed tumor cells to the non-human animal. In a specific embodiment, using the A2780 transformed cells according to the invention and in particular using the ovarian carcinoma cells deposited at BCCM with accession numbers LMBP 5958CB or LMBP 5959CB, a caliper measurable tumor is obtained 12 days after the injection of the cells.

Accordingly, in a further embodiment, the present invention provides a method to produce a non-human in vivo animal model to identify compounds with anti-neoplastic activity, said method comprising the steps of;

administering tumor cells according to the invention to a non-human animal, wherein the stably transformed tumor cells according to the invention are typically administered as a tumor cell suspension comprising $10^6$ to $10^8$ cells which is injected under the skin of the non-human animal; and allowing the tumor cells sufficient time to form a tumor in said non-human animal, which in the particular embodiment using the ovarian carcinoma cells as outlined above, typically consists of 7-14 days, more preferably 9-12 days and in particular 12 days.

The non-human animal model obtainable following the above mentioned method may subsequently be used in an in vivo method to identify compounds with anti-neoplastic activity, said method comprising the steps of;

administering a potentially active compound to a non human animal according to the invention, preferably a nude mice injected with ovarian carcinoma cells as outlined above, wherein the potentially active compound may be administered through all clinically relevant routes of administration including intravenously, orally and intraperitoneally; and evaluate the effect of said potentially active compound on the tumor cells by measuring the expression of the reporter gene.

Throughout this description the terms "standard methods", "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLE 1

Material and Methods

Cell Culture and Reagents

A2780 cells (ATCC) were cultivated in RPMI 1640 medium supplemented with 10% FCS, 2 mM L-glutamine and gentamycine at 37° C. in a humidified incubator with 5% $CO_2$. HCT116 cells (ATCC) were cultivated in Mc Coy's 5a medium supplemented with 10% FCS, 2 mM L-glutamine and gentamycin at 37° C. in a humidified incubator with 5% $CO_2$. All cell culture solutions are provided by Gibco-BRL (Gaithersburg, Md.). Other materials are provided by Nunc.

Production of a 4500 kb p21 promoter fragment and 1300 kb p21 promoter fragment Genomic DNA was extracted from proliferating A2780 cells and used as template for nested PCR isolation of the p21 promoter. The first amplification was performed for 20 cycles at an annealing temperature of 55° C. using the oligonucleotide pair GAGGGCGCGGT-GCTTGG (SEQ ID No.2) and TGCCGCCGCTCTCTCACC (SEQ ED No.3) with the genomic DNA as template. The resulting 4.5 kb fragment containing the −4551 to +88 fragment relative to the TATA box was re-amplified with the oligonucleotides TCG GGTACCGAGGGCGCGGTGCTIGG (SEQ ID No.4) and ATACTCGAGTGCCGCCGCTCTCTCACC (SEQ ID No.5) for 20 cycles with annealing at 88° C. resulting in a 4.5 kb fragment and subsequently with the oligonucleotide pair TCGGGTACCGGTAGATGGGAGCGGATAGACACATC (SEQ ID No.6) and ATACTCGAGTGCCGCCGCTCTCTCACC (SEQ ID No.7) for 20 cycles with annealing at 88° C. resulting in a 1.3 kb fragment containing the −1300 to +88 fragment relative to the TATA box. The restriction sites XhoI and KpnI present in the oligonucleotides (underlined sequence) were used for subcloning.

p21 Promoter Construct

The luciferase reporter was removed from the pGL3-basic and replaced by the ZsGreen reporter (from the pZsGreen1-N1 plasmid) at KpnI and XbaI restriction sites. pGL3-basic-ZsGreen-1300 was constructed via insertion of the above mentioned 1.3 kb fragment of the human p21 promoter region into pGL3-basic-ZsGreen at the XhoI and KpnI sites. All restriction enzymes are provided by Boehringer Manheim (Germany).

Transient Transfection and Stable Transfection

A2780 cells were plated into a 6-well plate at a density of $2×10^5$ cells, incubated for 24 hours, and transfected with 2 ug of pGL3-basic-ZsGreen-1300 and 0.2 ug of pSV2neo vector by using Lipofectamine 2000 (Invitrogen, Brussels, Belgium) as described by manufacturer. The transfected cells were selected for 10 days with G418 (Gibco-BRL, Gaithersburg, Md.) and single cell suspensions were grown. After three weeks, 80 single clones were obtained.

Induction of p21 Promoter Activity

The A2780 transfected pool and the selected 80 clones were expanded and seeded at 10000 cells per well into 96-well plates. 24 hours after seeding, the cells were treated for an additional 24 hours with targeted compounds (affecting sp1 sites in the proximal p21 promoter region) or DNA damaging agents (affecting p53 responsive elements). Subsequently, cells were fixed with 4% PFA for 30' and counterstained with Hoechst dye. The p21 promoter activation leading to ZsGreen production and thus fluorescence, was monitored by the Ascent Fluoroskan (Thermo Labsystems, Brussels, Belgium) and by fluorescence microscope (Zeiss).

In vivo Evaluation

The selected clone was injected subcutaneous ($10^7$ cells/200 µl) into the flank of nude mice and a calliper measurable tumor was obtained after 12 days. From day 12 on, animals were orally dosed daily during 6 days with solvent, 20 mpk Mitsui (a.k.a. MS-275—Shering—Registry Number 209783-80-2) or 40 mpk compound X (10, 10 and 4 animals respectively). Tumors were evaluated for fluorescence by the in-house developed Automated Whole Body Imaging System (Fluorescent stereomicroscope type Olympus® SZX12 equipped with a GFP filter and coupled to a CCD camera type JAI® CV-M90 controlled by a software package based on the IMAQ Vision Software from National Instruments®).

Results

Induction of p21 1300 bp Promoter Fragment by HDAC Inhibitors in vitro

A2780 stable transfected pool and the selected 80 clones were treated with TSA ($10^{-7}$ M), Bleomycin (15 mU) and Mitsui ($10^{-6}$ M) as described in M&M. Out of 80 clones 6 clones responded to TSA and Mitsui treatment. Four of these clones showed such a low basal fluorescence expression that they were not detectable with the Fluoroskan, but could be selected by manual evaluation of ZsGreen production using the fluorescence microscope. The two other clones could be measured and showed a 5 fold induction by TSA ($10^{-7}$) and a 1.2-1.5 fold by Mitsui ($10^{-6}$).

Figure 1:
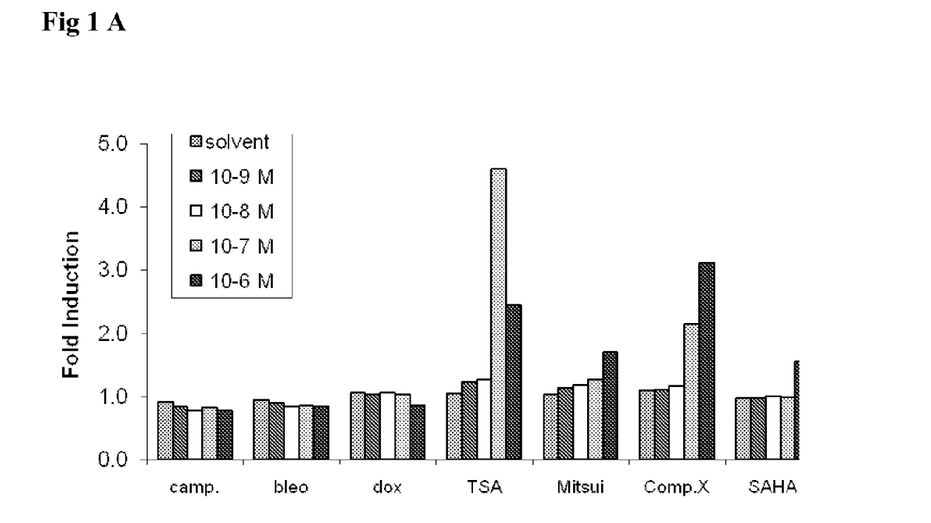

These 6 clones were evaluated in a dose response to DNA damaging agents (Camptothecin, Bleomycin and Doxorubicin) and HDAC inhibitors (TSA, Mitsui, Compound X, and Saha). Clone 1 showed a 5-fold induction in response to $10^{-7}$ TSA, 1.8 fold to $10^{-6}$ M Mitsui and 3 fold to $10^{-6}$M compound X (FIG. 1). DNA damaging agents were not able to activate the 1300 bp fragment of the p21 promoter (FIG. 1). Clone 5 showed identical responses (FIG. 1). The induction of clone 2, 3, 4 and 6 could not be measured by the Fluoroskan due to sensitivity problems of the system, but increase in fluorescence could be visualized by using the fluorescence microscope (data not shown).

Induction of p21 Promoter by HDAC Inhibitors in vivo

Figure 2:
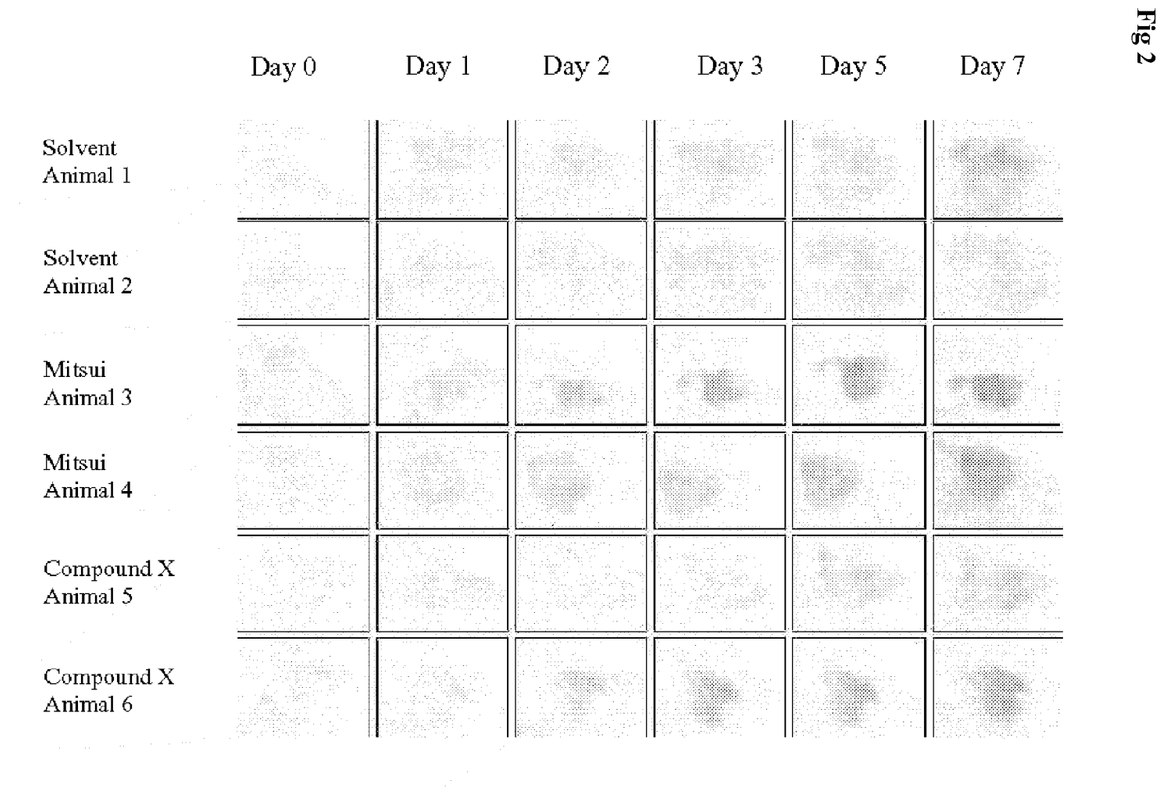

The mice were injected with clones 1, 2, 3 and 5 and dosed with compound (solvent, 20 mpk Mitsui or 40 mpk compound X) as described in M&M. Basal ZsGreen expression and induction were too low in clone 2 and 3 to be detected by Automated Whole Body Imaging System. Basal fluorescence of clone 1 and 5 could be measured and induction of ZsGreen was very clear 3 days after administration of the first dose and reached a plateau after 5 days (FIG. 2).

DISCUSSION

It has been shown that several known histone deacetylase inhibitors such as TSA, Mitsui and SAHA, induce transactivation of the murine p21$^{waf1,\ cip1}$ promoter through the −60 bp to +40 bp region relative to the TATA box. This region is present in our p21$^{waf1,\ cip1}$ 1300 bp promoter construct. Our data confirm that these agents induce ZsGreen production in the pGL3-basic-ZsGreen-1300 transfected A2780 cells in vitro. DNA damaging agents (Campthotecin, bleomycin and doxorubicin) excert their activity via p53 dependent regulation of p21$^{waf1,\ cip1}$ promoter. The p53 responsive elements are located more downstream in the p21$^{waf1,\ cip1}$ promoter at regions not present in the 1300 bp promoter fragment. This explains the non-responsivness of the system to DNA damaging agents. From these data we conclude that our reporter system provides a model for investigating the molecular events concerned with histone deacetylation and reveals the specificity of the reporter system in vitro. This concept can also be used to test DNA damaging agents specifically or any other drug by adapting the responsive element.

The in vivo action of a compound is much more complex and needs labor intensive animal studies to determine if the compound gets into circulation, reaches the tumor in an active form and if the concentration within the tumor is high enough to exerts its biological activity. It has been shown in more complicated PK/PD studies that the Mitsui compound can reach the tumor and that the concentration reached in the tumor is high enough to stop the tumor from growing. In this report, we show that the Mitsui compound induces fluorescence in the pGL3-basic-ZsGreen-1300 transfected A2780 xenograft after 4 days of treatment, implying that the compound reaches the tumor and exerts its biological activity in vivo. This confirms that this systems is a very power-full in vivo tool allowing fast and accurate conclusions on activity in vivo, allowing compounds to be evaluated at earlier time points in the drug discovery process without performing time and compound consuming PK/PD studies.

EXAMPLE 2

Material and Methods

Cell Culture and Reagents

A2780 cells (ATCC) were cultivated in RPMI 1640 medium supplemented with 10% FCS, 2 mM L-glutamine and gentamycin at 37° C. in a humidified incubator with 5% $CO_2$. HCT116 cells (ATCC) were cultivated in Mc Coy's 5a medium supplemented with 10% FCS, 2 mM L-glutamine and gentamycin at 37° C. in a humidified incubator with 5% $CO_2$. All cell culture solutions are provided by Gibco-BRL (Gaithersburg, Md.). Other materials are provided by Nunc.

Production of a p53 Responsive Element

The following oligo's p53RE forward CCCTGCCTG-GACTTGCCTGG GTCGACCCTGCCTGGACTTGCCTGGC (SEQ ID No.8) and p53RE reverse TCGAGCCAGGCAAGTCCAG-GCAGGGTCGACCCAGGCAAGTCCAG-GCAGGGAGCT (SEQ ID No.9) were ordered from Eurogentec. The oligonucleotide pair was annealed by a stepwise decrease of the annealing temperature every 5 minutes starting with 65° C. over 50° C., 40° C., 30° C. to a final temperature of 20° C. in annealing buffer (150 mM tris pH7,6, 15 mM $MgCl_2$, 23 mM DTT). A fragment with SacI/XhoI overhangs, for cloning purposes, was formed (responsive element is underlined sequence) (SEQ ID No.10):

TC<u>CCCTG CCTGGACTTG CCTGGGTCGA CCCTGCCTGG</u> ACTTGCCTGG C

CTCGAGGGAC GGACCTGAAC GGACCCAGCT GGGACGGACC TGAACGGACC GAGCTC

Construct

The luciferase reporter was removed from the pGL3-basic and replaced by the ZsGreen reporter (from the pZsGreen1-N1 plasmid) at KpnI and XbaI restriction sites.

The HSV-TK minimal promoter (thymidine kinase basal promoter of the herpes simplex virus) was obtained by PCR, the pTK Luc plasmid (Clontech # 6252-1) was used as the template. Primers were designed to amplify the HSV-TK minimal promoter together with the multiple cloning site of the pTK Luc plasmid. The amplification was performed for 30 cycles at an annealing temperature of 58° C. using the oligonucleotide pair GTACC<u>GAGCTC</u>TTACGCGTG (SEQ ID No. 11) and GT<u>GGATCC</u>CTGCTTCATCCCCGTGGC (SEQ ID No. 12) with the plasmid as template. The Expand High Fidelity PCR system was provided by Roche. The restriction sites SacI and BamHI present in the oligonucleotides (underlined sequence) were used for subcloning. Via insertion of the above mentioned 197 bp PCR fragment into the pGL3-basic-ZsGreen1-N1 at the SacI/BglII sites, the construct TK/pGL3-basic-ZsGreen was constructed. All restriction enzymes are provided by Roche (Germany).

The p53 responsive element was then cloned, in the SacI/XhoI cloning sites of the TK/pGL3-basic-ZsGreen vector, in front of the TK promoter to obtain the construct p53RE_TK/pGL3-basic-ZsGreen (FIG. 6).

Stable Transfection

A2780 cells and HCT116 cells were plated into a 6-well plate at a density of 4×10⁵ cells, incubated for 24 hours, and transfected with 2 ug of p53RE_TK/pGL3-basic-ZsGreen and 0.2 ug of pMC1-neo-Poly A vector by using Lipofectamine and Plus Reagent (Invitrogen, Brussels, Belgium) as described by manufacturer. The transfected cells were selected for 16 days with G418 (Gibco-BRL, Gaithersburg, Md.) and single cell suspensions were grown. After three weeks, 60 single clones were obtained from the transfected HCT116 cells and 40 single clones were obtained from the transfected A2780 cells.

Induction of p53RE_tk Activity

The A2780 and the HCT116 transfected pool and the selected clones were expanded and seeded at 20000 cells per well into 96-well plates. 24 hours after seeding, the cells were treated for an additional 24 hours with DNA damaging agents (affecting p53 responsive elements). The p53RE_tk activation leading to ZsGreen production and thus fluorescence, was monitored by the Ascent Fluoroskan (Thermo Labsystems, Brussels, Belgium) and by fluorescence microscope (Zeiss).

Results

Induction of p53RE_tk by a DNA Damaging Agent in vitro

Figure 3:
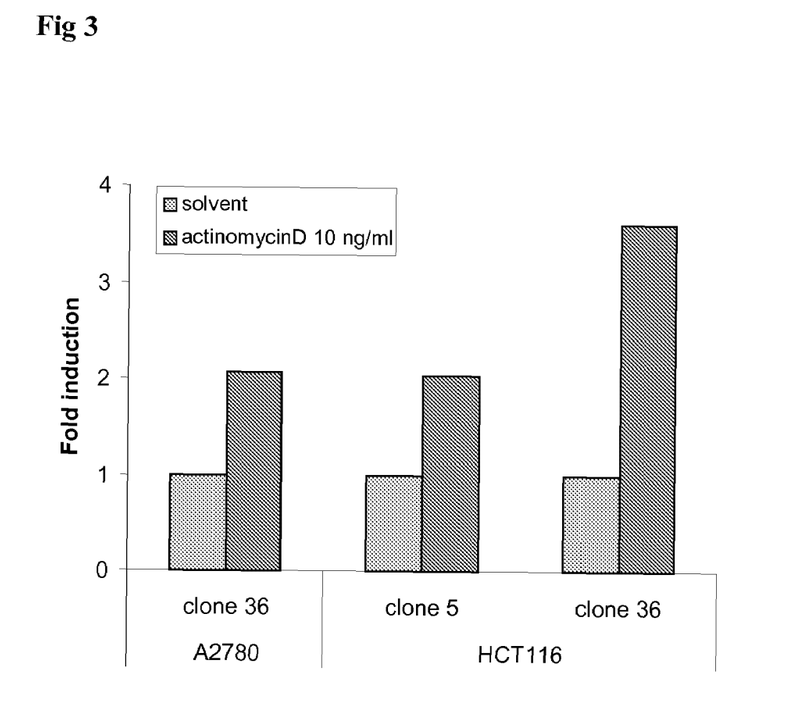
FIG. 3. Response of the p53RE promoter construct to the DNA damaging agent actinomycin D in A2780 and HCT116 clones. Cells are treated for 24 h with actinomycin D. Fluorescence was measured using the Fluoroskan as described in example 2. Fold induction was calculated as fluorescence after induction divided by fluorescence of DMSO treated cells. A2780 clone 36 showed a 2-fold induction after treatment with 10 ng/ml actinomycin D; a 2- to almost 4-fold induction was observed with the HCT116 clones.
Figure 4:
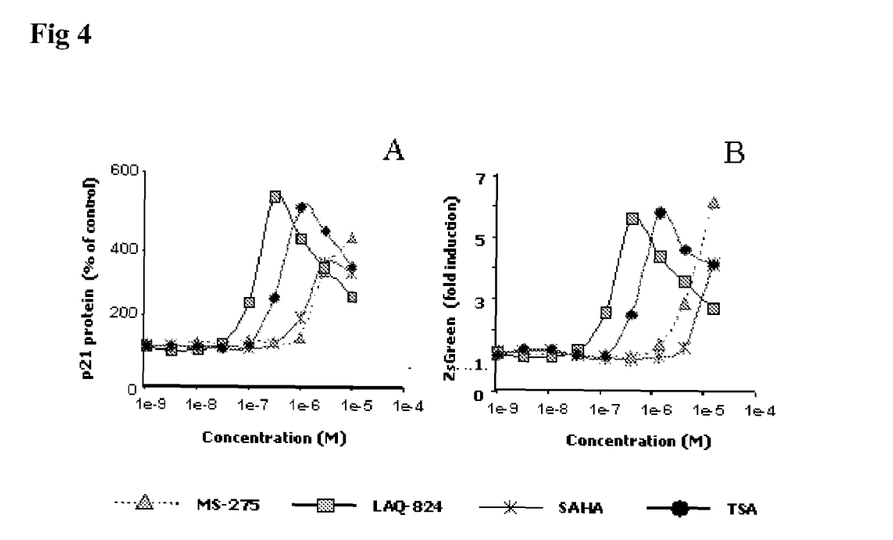
FIG. 4. $p21^{waf,cip1}$ promoter-ZsGreen model predicts the biological effect of HDAC inhibitors in vitro. Clone 5 of the A2780 ovarian tumor cells transfected with pG13-basic-ZsGreen-1300 were treated for 24 hours with the indicated concentrations of the HDAC inhibitors SAHA (*), MS-275 (Δ), LAQ-824 ( ) and TSA (●), or with solvent (0.1% DMSO).
Figure 5:
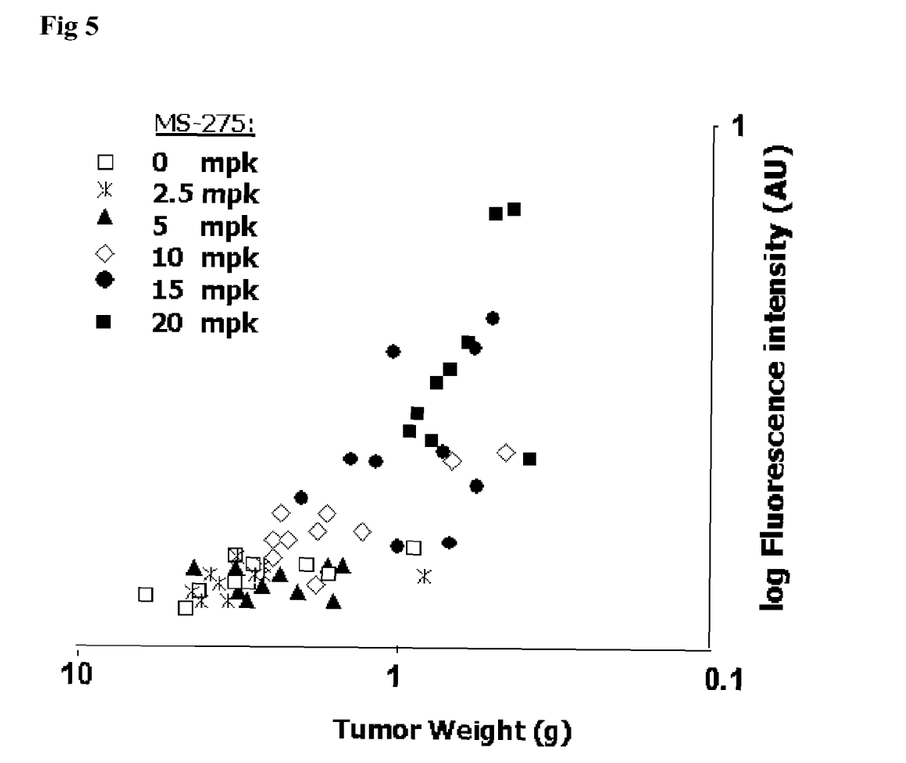

HCT116 and A2780 stable transfected pool and the selected clones were treated with actinomycinD (10 ng/ml). Out of the selected clones 6 HCT116 clones and 2 A278o clones responded to actinomycinD treatment. For these 8 clones, at least a two fold induction of fluorescence was detectable with the Fluoroskan in response to the treatment. In particular A2780 clone 36 and HCT116 clones 5 and 36 showed a detectable low basal fluorescence expression with a strong induction factor in response to actinomycin treatment (FIG. 3).

What is claimed is:

1. A stably transformed tumor cell capable of being employed in vivo comprising an expression vector containing a reporter gene operably linked to a promoter, wherein said stably transformed tumor cell is responsive to histone deacetylase inhibitors and not responsive to DNA damaging agents wherein said promoter consists of a human p21$^{WAF1/CIP-1}$ promoter fragment defined by SEQ ID NO: 1.

2. A stably transformed tumor cell according to claim 1 wherein the stably transformed tumor cells consist of stably transformed ovarian carcinoma cells.

3. A stably transformed tumor cell according to claim 1 wherein the reporter gene consists of a fluorescent protein.

4. An in vitro method of screening a candidate compound for anti-neoplastic activity, comprising the steps of: contacting the tumor cells of claim 1 with the candidate compound to be tested; comparing the reporter gene expression level in said tumor cells treated with said candidate compound to control cells; wherein an increase in expression level in said tumor cells treated with the candidate compound indicates that said candidate compound has anti-neoplastic activity.

* * * * *